United States Patent
Stitzel, Jr. et al.

(10) Patent No.: US 11,684,314 B2
(45) Date of Patent: Jun. 27, 2023

(54) ORAL INSERT AND USES THEREOF FOR CALCULATING FORCES TO THE HEAD

(71) Applicant: Ocellus, LLC, Winston-Salem, NC (US)

(72) Inventors: Joel Douglas Stitzel, Jr., Winston-Salem, NC (US); Michael Hurst, Winston-Salem, NC (US); Jillian Urban Hobson, Winston-Salem, NC (US)

(73) Assignee: Ocellus, LLC, Winston-Salem, NC (US)

( * ) Notice: Subject to any disclaimer, the term of this patent is extended or adjusted under 35 U.S.C. 154(b) by 462 days.

(21) Appl. No.: 16/493,444

(22) PCT Filed: Mar. 23, 2018

(86) PCT No.: PCT/US2018/023929
§ 371 (c)(1),
(2) Date: Sep. 12, 2019

(87) PCT Pub. No.: WO2018/175835
PCT Pub. Date: Sep. 27, 2018

(65) Prior Publication Data
US 2020/0008744 A1    Jan. 9, 2020

Related U.S. Application Data

(60) Provisional application No. 62/475,760, filed on Mar. 23, 2017.

(51) Int. Cl.
*A61B 5/00* (2006.01)
*A61B 5/11* (2006.01)
(Continued)

(52) U.S. Cl.
CPC ............ *A61B 5/682* (2013.01); *A61B 5/1116* (2013.01); *A61B 5/4064* (2013.01);
(Continued)

(58) Field of Classification Search
CPC ..... A61B 5/682; A61B 5/1116; A61B 5/4064; A61B 2503/10; A61B 2562/0219;
(Continued)

(56) References Cited

U.S. PATENT DOCUMENTS

| | | |
|---|---|---|
| 4,629,424 A | 12/1986 | Lauks et al. |
| 5,490,520 A | 2/1996 | Schaefer et al. |

(Continued)

FOREIGN PATENT DOCUMENTS

WO    2011/153175    12/2011

OTHER PUBLICATIONS

U.S. Appl. No. 15/205,791, Final Office Action, dated Jul. 27, 2020, 7 pages.
(Continued)

*Primary Examiner* — Patrick Fernandes
(74) *Attorney, Agent, or Firm* — Kilpatrick Townsend & Stockton LLP

(57) ABSTRACT

The present disclosure generally provides oral inserts useful for determining forces experienced by a user, such as a human user, to the head, for example, by measuring one or more of acceleration, velocity, displacement, or rotation. In some aspects, the disclosure provides oral inserts that, when worn properly by a human user, calculate the forces experienced by the user's head with high accuracy. In some aspects, the disclosure provides systems for detecting and calculating forces experienced by the user's head and to determine whether such forces are above a certain threshold indicative of increased concussion risk. In some aspects, the disclosure provides methods for calculating forces experi-
(Continued)

enced by the user's head and determining whether such forces are above a certain threshold indicative of concussion.

17 Claims, 8 Drawing Sheets

(51) Int. Cl.
    *A63B 71/08*                    (2006.01)
    *A63B 71/10*                    (2006.01)

(52) U.S. Cl.
    CPC ............ *A63B 71/085* (2013.01); *A63B 71/10* (2013.01); *A61B 2503/10* (2013.01); *A61B 2562/0219* (2013.01); *A63B 2220/40* (2013.01); *A63B 2220/53* (2013.01); *A63B 2220/836* (2013.01)

(58) Field of Classification Search
    CPC ..... A61B 5/4557; A63B 71/085; A63B 71/10; A63B 2220/40; A63B 2220/53; A63B 2220/836; A61C 9/0006; A61N 1/325; A61N 1/0548

See application file for complete search history.

(56) References Cited

U.S. PATENT DOCUMENTS

| | | | |
|---|---|---|---|
| 5,523,745 | A | 6/1996 | Fortune et al. |
| 6,941,952 | B1 | 9/2005 | Rush |
| 7,890,193 | B2 | 2/2011 | Tingey |
| 7,995,031 | B2 | 8/2011 | Manal |
| 8,453,650 | B1 | 6/2013 | Frey |
| 8,666,738 | B2 | 3/2014 | Moeller |
| 9,226,707 | B2 | 1/2016 | Huang |
| 9,301,061 | B2 | 3/2016 | Mersky |
| 9,402,998 | B2 | 8/2016 | Davidovitch et al. |
| 9,504,417 | B2 | 11/2016 | Shimoyama et al. |
| 9,526,289 | B2 | 12/2016 | Mack et al. |
| 9,549,841 | B2 | 1/2017 | Hermanson et al. |
| 9,955,918 | B2 | 5/2018 | Paris et al. |
| 10,172,555 | B2 | 1/2019 | Cam et al. |
| 2002/0144691 | A1* | 10/2002 | Kittelsen .............. A63B 71/085 128/861 |
| 2005/0256276 | A1* | 11/2005 | Elkin ................... A61C 9/0006 525/400 |
| 2007/0085827 | A1 | 4/2007 | Sturtz |
| 2009/0078274 | A1 | 3/2009 | Bhat et al. |
| 2009/0130635 | A1 | 5/2009 | Tortorici |
| 2010/0286587 | A1* | 11/2010 | Gross ..................... A61N 1/325 604/20 |
| 2011/0027743 | A1 | 2/2011 | Cinader, Jr. et al. |
| 2011/0270053 | A1 | 11/2011 | Utley et al. |
| 2012/0240941 | A1 | 9/2012 | Rosenman et al. |
| 2014/0134561 | A1 | 5/2014 | Smith et al. |
| 2014/0188010 | A1* | 7/2014 | Paris .................... A61B 5/1126 600/595 |
| 2014/0257051 | A1 | 9/2014 | Cam et al. |
| 2015/0057719 | A1 | 2/2015 | Tang |
| 2015/0190630 | A1 | 7/2015 | Kent et al. |
| 2015/0238142 | A1* | 8/2015 | Djordjevski ......... A61B 5/4547 600/587 |
| 2015/0290453 | A1 | 10/2015 | Tyler et al. |
| 2015/0305671 | A1 | 10/2015 | Yoon et al. |
| 2015/0374274 | A1 | 12/2015 | Jovanovski |
| 2017/0095204 | A1 | 4/2017 | Stitzel et al. |

OTHER PUBLICATIONS

U.S. Appl. No. 15/205,791, Non-Final Office Action, dated Mar. 25, 2021, 11 pages.
U.S. Appl. No. 15/205,791 , "Final Office Action", dated Sep. 27, 2018, 7 pages.
U.S. Appl. No. 15/205,791 , "Non-Final Office Action", dated Dec. 6, 2019, 7 pages.
U.S. Appl. No. 15/205,791 , "Restriction Requirement", dated Jun. 21, 2018, 6 pages.
U.S. International Search Report and Written Opinion for PCT/US2018/023929 dated May 21, 2018.
U.S. Appl. No. 15/205,791, Advisory Action, dated Dec. 10, 2021, 6 pages.
U.S. Appl. No. 15/205,791, Final Office Action, dated Sep. 21, 2021, 14 pages.
U.S. Appl. No. 15/205,791, Non-Final Office Action, dated Feb. 17, 2022, 10 pages.

* cited by examiner

ORAL INSERT AND USES THEREOF FOR CALCULATING FORCES TO THE HEAD

CROSS-REFERENCE TO RELATED APPLICATIONS

The present application claims the benefit of priority of PCT Application PCT/US2018/023929, filed Mar. 23, 2018, which claims the benefit of priority of U.S. Provisional Application No. 62/475,760, filed Mar. 23, 2017, which are hereby incorporated by reference as though each is set forth herein in its entirety. In addition, the present application hereby incorporates by reference the entirety of U.S. patent application Ser. No. 15/205,791, filed Jul. 8, 2016, as though set forth herein in its entirety.

TECHNICAL FIELD

The present disclosure generally provides oral inserts useful for determining forces experienced by a user, such as a human user, to the head, for example, by measuring one or more of acceleration, velocity, displacement, or rotation. In some aspects, the disclosure provides oral inserts that, when worn properly by a human user, calculate the forces experienced by the user's head with high accuracy. In some aspects, the disclosure provides systems for detecting and calculating forces experienced by the user's head and to determine whether such forces are above a certain threshold indicative of increased concussion risk. In some aspects, the disclosure provides methods for calculating forces experienced by the user's head and determining whether such forces are above a certain threshold indicative of concussion.

DESCRIPTION OF RELATED ART

Mild traumatic brain injury (mTBI), also referred to as a concussion, is one of the most types of brain injury experienced by people. Although concussions can result from a variety of events, including accidents and falls, they are especially common in certain sports that involve bumping of the head. Such sports include football (American), soccer, rugby, lacrosse, and the like. When players experience such an injury, it is important that they receive treatment and sufficient opportunity to allow the brain to recover. Therefore, diagnosing and detecting such injuries is vital to maintaining the health of athletes who participate in sports where the potential for experiencing head impact is high.

In most cases, mTBI is measured via physical examination by a medical professional. But mTBI is difficult to detect merely based on a sideline physical examination. In many cases, the players may be in the best position to assess whether or not they have experienced mTBI. Therefore, diagnosis often depends on players' willingness to provide accurate information concerning the symptoms they experience following an impact. But in the midst of a sporting event, players are prone to under-report their symptoms, either intentionally or unintentionally. Thus, a substantial number of cases of mTBI go undiagnosed, and players return to the field of play, placing themselves in danger of suffering further damage to their brain.

Various sensing devices have been developed to calculate the forces that players experience to their heads. For example, one such device attaches to the neck of the user. While this device overcomes some of the problems associated with sideline physical examination, it has its own problems. For example, skin on the neck often experiences acceleration in situations where the head may remain relatively stationary. This is especially true for athletes who may have a greater amount of adipose tissue in the neck area. Therefore, such devices are prone to show false positives. Another such device fits into the mouth and has a sensor that protrudes beyond the teeth. And while such a design overcomes some of the issues with skin movement, it too has a tendency to show false positives and provide inaccurate measurement of acceleration due to poor correlation between the acceleration measured by the device and the acceleration actually experienced by the user's head. Another device also fits into the mouth, but includes the sensor within a mouth guard structure that wraps around the teeth. For comfort and to allow for a snug fit around the teeth, the guard is made of an elastic material. But this device tends to degrade over time, as the elastic material is worn down by the constant contact with the teeth. Some players have a tendency to bite and chew on the device, which eventually causes the material to degrade and necessitates replacement. Moreover, as the mouth guard wears down, it can move within the mouth to a greater degree and lose its ability to make accurate calculations of impact forces.

Thus, there is a continuing need to develop improved devices for detecting and calculating the forces experienced by a person's head during physical activities in which head contact is common.

SUMMARY

The present disclosure provides, among other things, an oral insert that overcomes one or more of the deficiencies of prior devices, and allows for a more durable apparatus, increased accuracy of measurement, fewer false positives, and, in some instances, improved comfort for the user, especially in the context of sports-related activities.

In a first aspect, the disclosure provides oral inserts for measuring head motion, the insert comprising: a first insert surface configured to contact a first surface of a user's mouth, wherein the first surface of the user's mouth comprises the interior surface of one or more teeth of the upper left side of the user's mouth or the interior surface of the gums of upper left side of the user's mouth; a second insert surface configured to contact a second surface of the user's mouth, wherein the second surface of the user's mouth comprises the interior surfaces of one or more teeth of the upper right side of the user's mouth or the interior surface of the gums of the upper right side of the user's mouth; a connecting structure, which is in physical communication with the first insert surface and the second insert surface via the posterior side of the first insert surface and the posterior side of the second insert surface; and a sensing device, wherein the sensing device is in physical communication with the connecting structure.

In a second aspect, the disclosure provides systems for calculating force experienced by the head of a user, which include an oral insert of the first aspect. In some embodiments, the systems include a processor that determines whether the force calculated by the oral insert is indicative of a user's having experienced a concussion or increased risk thereof.

In a third aspect, the disclosure provides methods for calculating force experienced by the head of a user, which include: providing an oral insert of the first aspect; inserting the oral insert securely behind the upper teeth of a user at a first time; receiving data from the oral insert at a second time, which is later than the first time; and analyzing the data to determine the force experienced by the user from the first time to the second time. In some embodiments, the methods include determining whether the force calculated by the oral insert is indicative of a user's having experienced a concussion or increased risk thereof.

In a fourth aspect, the disclosure provides methods for assessing the effectiveness of a safety system, the methods comprising: providing an oral insert of any one of the foregoing aspects and embodiments; disposing the oral insert securely to the head of a test subject; protecting the test subject with a safety system; and applying an external force to the test subject while protected with the safety system; and determining the force experienced by the head of the test subject due to the applying of the external force.

In a fifth aspect, the disclosure provides methods for assessing the risk of a procedure for carrying out an activity, the method comprising: providing an oral insert of any of the foregoing aspects and embodiments; disposing the oral insert securely to the head of a test subject; employing the test subject to carry out an activity according to a procedure; and applying an external force to the test subject while carrying out the activity; and determining the force experienced by the head of the test subject due to the applying of the external force.

Further aspects and embodiments are provided in the drawings, the detailed description, the claims, and the abstract.

BRIEF DESCRIPTION OF DRAWINGS

The following drawings are provided for purposes of illustrating various embodiments of the compounds, compositions, methods, and uses disclosed herein. The drawings are provided for illustrative purposes only, and are not intended to describe any preferred compounds or compositions or any preferred methods or uses, or to serve as a source of any limitations on the scope of the claimed inventions.

DETAILED DESCRIPTION

Figure 1:
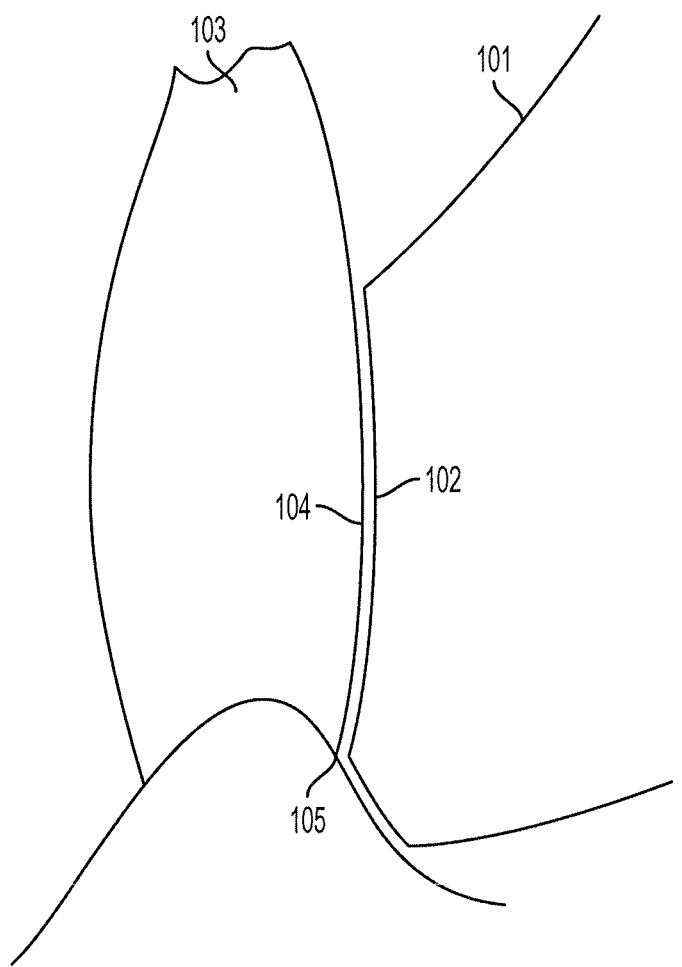
FIG. 1 shows a non-limiting example of the placement of the oral insert having a surface in contact with a portion of the interior surface of a upper tooth of the left side of the user's mouth, with the view from the rear of the mouth.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, the term "user" refers to an animal. In some embodiments, the user is a mammal. In some such embodiments, the user is a human.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present. As used herein, the phrases "consist essentially of" "consists essentially of" and "consisting essentially of" refer to groups that are open, but which only includes additional unnamed members that would not materially affect the basic characteristics of the claimed subject matter.

As used herein, "or" is to be given its broadest reasonable interpretation, and is not to be limited to an either/or type of construction. Thus, the phrase "comprising A or B" means that A is present and not B, that B is present and not A, or that A and B are both present. Further, if A, for example, defines a class that can have multiple members, e.g., $A_1$ and $A_2$, then one or more members of the class can be present concurrently.

All ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g., 1 to 6.1, and ending with a maximum value of 10 or less, e.g., 5.5 to 10.

Other terms are defined in other portions of this description, even though not included in this subsection.

Oral Inserts

In at least one aspect, the disclosure provides oral inserts for measuring head motion, the inserts comprising: a first insert surface configured to contact a first surface of a user's mouth, wherein the first surface of the user's mouth comprises the interior surface of one or more teeth of the upper left side of the user's mouth or the interior surface of the gums of upper left side of the user's mouth; a second insert surface configured to contact a second surface of the user's mouth, wherein the second surface of the user's mouth comprises the interior surfaces of one or more teeth of the upper right side of the user's mouth or the interior surface of the gums of the upper right side of the user's mouth; a connecting structure, which is in physical communication with the first insert surface and the second insert surface via the posterior side of the first insert surface and the posterior side of the second insert surface; and a sensing device, wherein the sensing device is in physical communication with the connecting structure.

In some embodiments of this aspect, the user is a mammal. In some further such embodiments, the user is a human, including children, adolescents, and adults, and both biological males and females. Further, as used herein, the "interior surface" of the teeth or gums refers to the surfaces facing inward, which are sometimes referred to as the lingual surfaces.

In embodiments of this aspect, the first insert surface configured to contact a first surface of a user's mouth, wherein the first surface of the user's mouth comprises the interior surface of one or more teeth of the upper left side of the user's mouth or the interior surface of the gums of upper left side of the user's mouth.

In this context, where the insert is designed to be used an environment where saliva is present, the term "contact" contemplates that a thin layer of saliva is, in most instances, present on both the surfaces of the user's teeth and gums and on the surfaces of the insert when the insert is in use. Further, in this context, the phrase "configured to" describes a structural feature the first insert surface such that it has a shape or contour that permits it to maintain persistent contact with the first surface of the user's mouth. The first insert surface and the first surface of the user's mouth have no minimum size. Moreover, the surfaces of the user's teeth or gums do not necessarily refer to the entire surface of said teeth or gums; it is sufficient that the first insert surface contact at least a portion of the surfaces of two or more teeth or contact at least a portion of the gum. In some embodiments, the first insert surface is a rigid surface, e.g., a surface that does not conform to take on the shape of surfaces of the user's mouth. Therefore, configuring the surface to contact certain surfaces of a user's mouth generally involves measuring the contours of certain surfaces of the user's mouth (e.g., by a dental mold) and forming the first insert surface to have a shape that fits to said contours.

The first insert surface and the corresponding first surface of the user's mouth can include any suitable portion of the surfaces of the teeth or gums. Of course, the insert can, in some embodiments, include surfaces, including surfaces contiguous with the first surface, that contact other portions of the user's mouth. In some embodiments, the first surface of the user's mouth comprises the interior surface of one or more teeth of the upper left side of the user's mouth. In some embodiments, the first surface of the user's mouth comprises the interior surface of the gums of the upper left side of the user's mouth. In some further such embodiments, the first surface of the user's mouth comprises the interior surface of one or more teeth of the upper left side of the user's mouth and the interior surface of the gums of the upper left side of the user's mouth. In some such embodiments, said interior surfaces of one or more teeth are immediately adjacent to said interior surface of the gums. In some further such embodiments, the first surface of the user's mouth comprises the interior surface of two or more, or three or more, or four or more teeth of the upper left side of the user's mouth. In some further such embodiments, the first surface of the user's mouth comprises a portion of the interior surface of the first bicuspid, or a portion of the interior surfaces of the first bicuspid and the second bicuspid, or a portion of the interior surfaces of the first bicuspid, the second bicuspid, and the left canine tooth. In some embodiments of any of the aforementioned embodiments, the first insert surface is configured to extend into at least a portion of the interproximal space between two teeth.

In some embodiments where the first insert surface contacts the surfaces of one or more teeth, the insert is configured to contact certain portions of said one or more teeth. Human teeth generally have a convex contour, such that the tooth is thicker midway along its length than it is at its base or cap. This maximal point of this convex bulge is called the "height of contour." Due to the presence of this feature, the teeth have a natural design that allows one to "click" closely contoured objects into place. In some cases, this can assist in helping to keep the insert in place without requiring the insert to exert an expansive force against the teeth. Thus, in some embodiments of any of the aforementioned embodiments, the first surface of the user's mouth includes at least a portion of the surface(s) of one or more, two or more, or three or more, of the user's teeth between the height of contour of said teeth and the gum line. Because the first insert surface is configured to contact such surfaces, this allows the insert to "click" into place when inserted into the mouth of a user.

It can also be important for the first insert surface to maintain snug contact at the transition point (or groove) between the one or more teeth and the gums. Therefore, in some embodiments of any of the aforementioned embodiments, the first insert surface is configured to contact the first surface of the user's mouth, wherein the first surface of the user's mouth includes, among other features, at least a portion of the transition line or groove between (and adjacent to) the one or more teeth and the gums.

FIG. 1 shows an example of at least one such embodiments, where the insert 101 has a first surface 102 that contacts at least a portion of the surface of a tooth 103 in the area between the height of curvature 104 and the gum line 105.

When two well adapted surfaces come together with a liquid layer between them, the liquid layer exerts a certain resistance to the separation of the two surfaces. This resistance to displacement of the two surfaces relative to each other is referred to as "interfacial surface tension." Because saliva is generally present in the mouth of mammals, such as humans, one can make use of such forces to assist in keeping an insert into place. Thus, in some embodiments of any of the aforementioned embodiments, the first insert surface is configured to maintain interfacial surface tension between at least a portion of the first insert surface and at least a portion of the first surface of the user's mouth. This can be accomplished by designing the rigid insert to have a first surface that conforms well to the contours of the first surface of the user's mouth. In such cases, it can also be desirable for the first insert surface to extend into the interproximal space between one or more pairs of teeth, so as to prevent air pockets from forming between the first insert surface and the first surface of the user's mouth. It can also be desirable for the first area of the insert (and the concomitant first surface of the user's mouth) to be larger, e.g., to include at least a portion of two or more, or three or more, or four or more teeth, and to extend into the interproximal space of one or more, two or more, or three or more pairs of teeth. One can also improve the retention of interfacial surface tension by including texture (non-smooth portions), such as grooves or abrasions, on at least a portion of the insert surface. Thus, in some embodiments of any of the aforementioned embodiments, at least a portion of the first insert surface comprises surface texture (or surface topography).

In some embodiments of any of the aforementioned embodiments, it can be desirable that the first insert surface exert a mild expansive (outward) force against the first surface of the user's mouth. This can assist in ensuring that the insert remains in place and maintains interfacial surface tension. Thus, in some embodiments, the first insert surface exerts an expansive force against the first surface of the user's mouth. This mild expansive force can be of any suitable quantity, bearing in mind that it should not be so strong as to cause the user discomfort or to prevent the user from easily removing the insert past the height of contour of the teeth. In some embodiments, the expansive force (as force per area) is no more than 50 mmHg, or no more than 40 mm Hg, or no more than 30 mm Hg, or no more than 25 mm Hg, or no more than 20 mm Hg, or no more than 10 mm Hg, or no more than 5 mm Hg. In some such embodiments, this expansive force is generated by compression or deformation of the connecting structure between the first insert surface and the second insert surface.

In embodiments of this aspect, the second insert surface is configured to contact a second surface of a user's mouth, wherein the second surface of the user's mouth comprises the interior surface of one or more teeth of the upper left side of the user's mouth or the interior surface of the gums of upper left side of the user's mouth.

In this context, where the insert is designed to be used an environment where saliva is present, the term "contact" contemplates that a thin layer of saliva is, in most instances, present on both the surfaces of the user's teeth and gums and on the surfaces of the insert when the insert is in use. Further, in this context, the phrase "configured to" describes a structural feature of the second insert surface such that it has a shape or contour that permits it to maintain persistent contact with the second surface of the user's mouth. The second insert surface and the second surface of the user's mouth have no minimum size. Moreover, the surfaces of the user's teeth or gums do not necessarily refer to the entire surface of said teeth or gums; it is sufficient that the second insert surface contact at least a portion of the surfaces of two or more teeth or contact at least a portion of the gum. In some embodiments, the second insert surface is a rigid surface, e.g., a surface that does not conform to take on the shape of surfaces of the user's mouth. Therefore, configuring the surface to contact certain surfaces of a user's mouth generally involves measuring the contours of certain surfaces of the user's mouth (e.g., by a dental mold) and forming the second insert surface to have a shape that fits to said contours.

The second insert surface and the corresponding second surface of the user's mouth can include any suitable portion of the surfaces of the teeth or gums. Of course, the insert can, in some embodiments, include surfaces, including surfaces contiguous with the second surface, that contact other portions of the user's mouth. In some embodiments, the second surface of the user's mouth comprises the interior surface of one or more teeth of the upper left side of the user's mouth. In some embodiments, the second surface of the user's mouth comprises the interior surface of the gums of the upper left side of the user's mouth. In some further such embodiments, the second surface of the user's mouth comprises the interior surface of one or more teeth of the upper left side of the user's mouth and the interior surface of the gums of the upper left side of the user's mouth. In some such embodiments, said interior surfaces of one or more teeth are immediately adjacent to said interior surface of the gums. In some further such embodiments, the second surface of the user's mouth comprises the interior surface of two or more, or three or more, or four or more teeth of the upper left side of the user's mouth. In some further such embodiments, the second surface of the user's mouth comprises a portion of the interior surface of the first bicuspid, or a portion of the interior surfaces of the first bicuspid and the second bicuspid, or a portion of the interior surfaces of the first bicuspid, the second bicuspid, and the left canine tooth. In some embodiments of any of the aforementioned embodiments, the second insert surface is configured to extend into at least a portion of the interproximal space between two teeth.

In some embodiments where the second insert surface contacts the surfaces of one or more teeth, the insert is configured to contact certain portions of said one or more teeth. As noted above, human teeth generally have a height of contour. Due to the presence of this feature, the teeth have a natural design that allows one to "click" closely contoured objects into place. In some cases, this can assist in helping to keep the insert in place without requiring the insert to exert an expansive force against the teeth. Thus, in some embodiments of any of the aforementioned embodiments, the second surface of the user's mouth includes at least a portion of the surface(s) of one or more, two or more, or three or more, of the user's teeth between the height of contour of said teeth and the gum line. Because the second insert surface is configured to contact such surfaces, this allows the insert to "click" into place when inserted into the mouth of a user.

It can also be important for the first insert surface to maintain snug contact at the transition point (or groove) between the one or more teeth and the gums. Therefore, in some embodiments of any of the aforementioned embodiments, the first insert surface is configured to contact the first surface of the user's mouth, wherein the first surface of the user's mouth includes, among other features, at least a portion of the transition line or groove between (and adjacent to) the one or more teeth and the gums.

Figure 2:
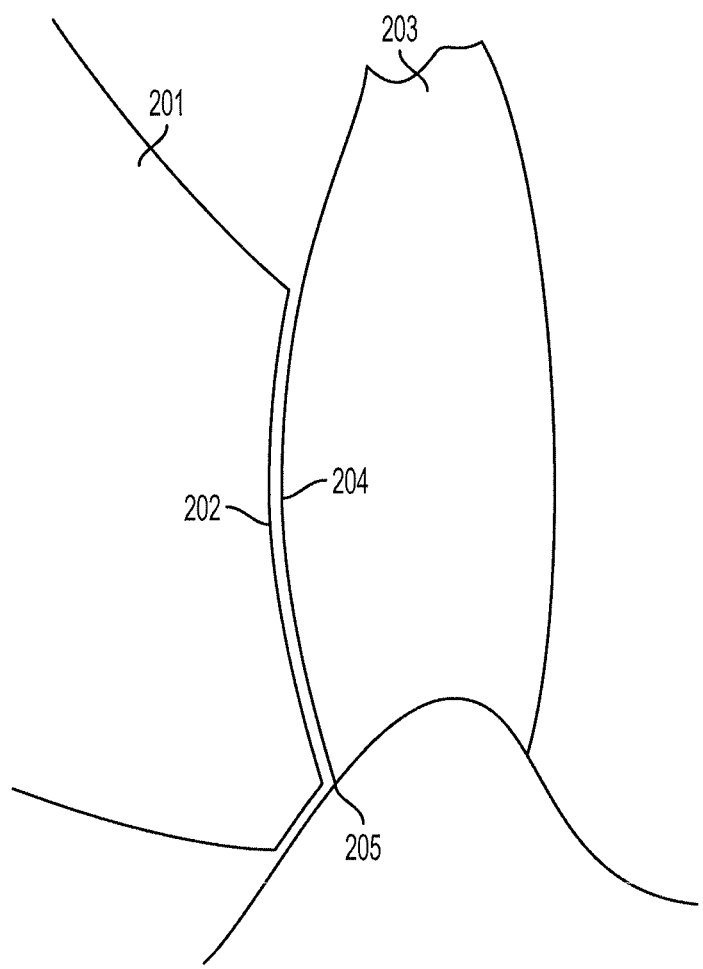
FIG. 2 shows a non-limiting example of the placement of the oral insert having a surface in contact with a portion of the interior surface of a upper tooth of the right side of the user's mouth, with the view from the rear of the mouth.

FIG. 2 shows an example of at least one such embodiments, where the insert 201 has a second surface 202 that contacts at least a portion of the surface of a tooth 203 in the area between the height of curvature 204 and the gum line 205.

As noted above, when two well adapted surfaces come together with a liquid layer between them, the liquid layer exerts a certain resistance to the separation of the two surfaces called interfacial surface tension. Because saliva is generally present in the mouth of mammals, such as humans, one can make use of such forces to assist in keeping an insert into place. Thus, in some embodiments of any of the aforementioned embodiments, the second insert surface is configured to maintain interfacial surface tension between at least a portion of the second insert surface and at least a portion of the second surface of the user's mouth. This can be accomplished by designing the rigid insert to have a second surface that conforms well to the contours of the second surface of the user's mouth. In such cases, it can also be desirable for the second insert surface to extend into the interproximal space between one or more pairs of teeth, so as to prevent air pockets from forming between the second insert surface and the second surface of the user's mouth. It can also be desirable for the second area of the insert (and the concomitant second surface of the user's mouth) to be larger, e.g., to include at least a portion of two or more, or three or more, or four or more teeth, and to extend into the interproximal space of one or more, two or more, or three or more pairs of teeth. One can also improve the retention of interfacial surface tension by including texture (non-smooth portions), such as grooves or abrasions, on at least a portion of the insert surface. Thus, in some embodiments of any of the aforementioned embodiments, at least a portion of the second insert surface comprises surface texture (or surface topography).

In some embodiments of any of the aforementioned embodiments, it can be desirable that the second insert surface exert a mild expansive (outward) force against the second surface of the user's mouth. This can assist in ensuring that the insert remains in place and maintains interfacial surface tension. Thus, in some embodiments, the second insert surface exerts an expansive force against the second surface of the user's mouth. This mild expansive force can be of any suitable quantity, bearing in mind that it should not be so strong as to cause the user discomfort or to prevent the user from easily removing the insert past the height of contour of the teeth. In some embodiments, the expansive force (as force per area) is no more than 50 mmHg, or no more than 40 mm Hg, or no more than 30 mm Hg, or no more than 25 mm Hg, or no more than 20 mm Hg, or no more than 10 mm Hg, or no more than 5 mm Hg. In some such embodiments, this expansive force is generated by compression or deformation of the connecting structure between the second insert surface and the second insert surface.

The above disclosure refers to a first insert surface and a second insert surface. This terminology does not imply that the two surfaces are necessarily discontinuous. For example, in some embodiments, the first insert surface and the second insert surface are part of a continuous surface, which, in some embodiments, is configured to contact at least a portion of the interior surfaces of all of the non-molar upper teeth. In some other embodiments, the first insert surface and the second surface are discontinuous. For example, in some such embodiments, the insert does not comprise a surface that contacts any portion of the interior surfaces of the left or right maxillary central incisors.

Also, as noted above, the first insert surface and second insert surface are, in some embodiments, rigid. In some such embodiments, the first insert surface and the second insert surface have a shore A hardness of at least 40, or a shore A hardness of at least 45, or a shore A hardness of at least 50, or a shore A hardness of at least 55, or a shore A hardness of at least 60, at 25° C. Note that materials that are more suited to hardness measurements using the shore D durometer or the Rockwell test are generally harder than the shore A values recited here, and are therefore included as having a hardness that meets these lower cut-offs. The description of this feature in terms of shore A hardness is not intended to limit the embodiment only to materials whose hardness is suitable for measurement using the shore A durometer.

Figure 3:
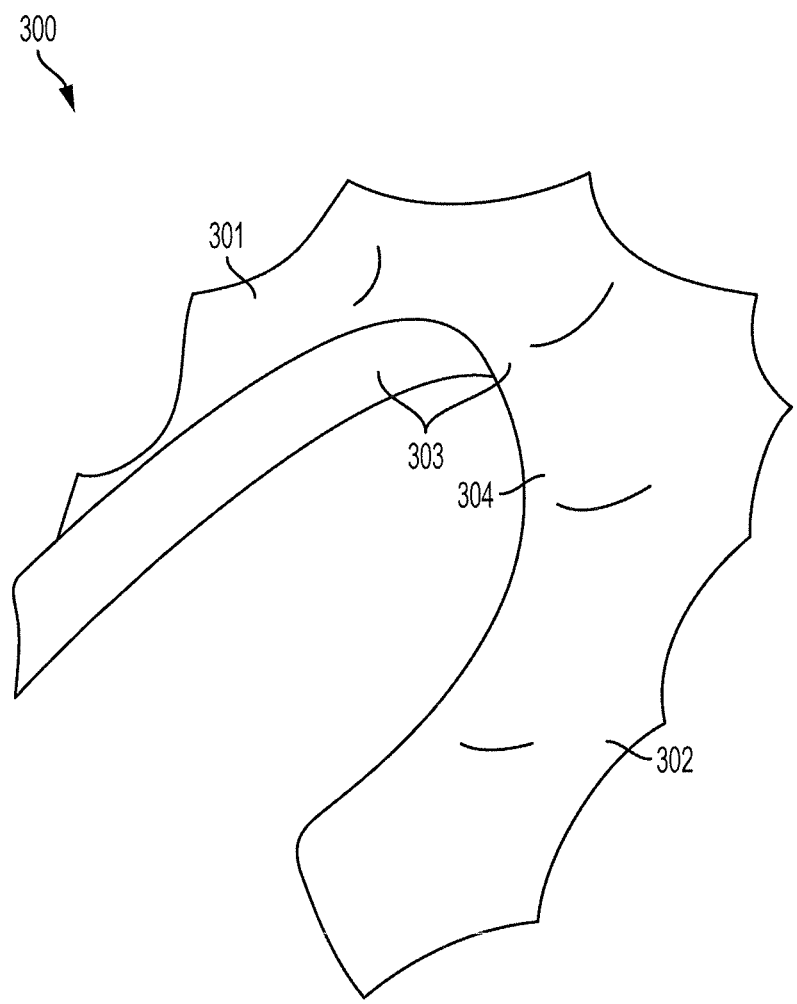
FIG. 3 shows a non-limiting example of an oral insert where the first insert surface and the second insert surface form a continuous surface.
Figure 4:
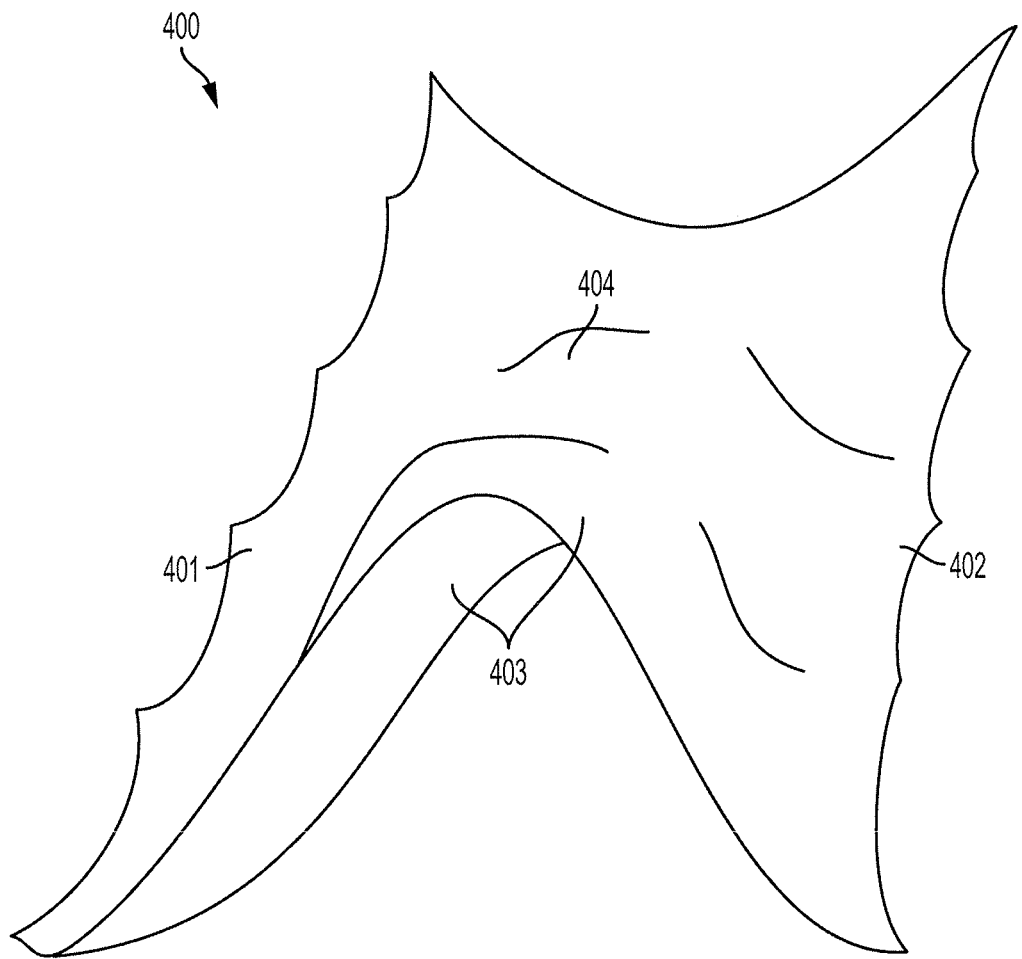
FIG. 4 shows a non-limiting example of an oral insert where the first insert surface and the second insert surface are discontinuous from each other.

In embodiments of this aspect, the insert comprises a connecting structure, which is in physical communication with the first insert surface and the second insert surface via the posterior side of the first insert surface and the posterior side of the second insert surface. The connecting structure can be any suitable structure that physically connects the first insert surface and the second insert surface from their respective posterior sides. For example, in some embodiments, where the first insert surface and the second insert surface are part of a continuous surface that contacts the interior surfaces of the upper non-molar teeth, the connecting structure is a structure that lies behind the insert surfaces and provides structural reinforcement. FIG. 3 shows such an insert 300 having a first insert surface 301 and a second insert surface 302 and a connecting structure 303 having a third insert surface 304 (described below). For example, in some other embodiments, where the first insert surface and the second insert surface are discontinuous, the connecting structure is a structure that bridges the distance between the posterior sides of the first insert surface and the second insert surface. FIG. 4 shows such an insert 400 having a first insert surface 401 and a second insert surface 402 and a connecting structure 403 having a third insert surface 404 (described below).

In some embodiments of any of the aforementioned embodiments, the connecting structure includes one or more surfaces that are configured to contact one or more portions of the user's mouth. This helps ensure that the connecting structure follows the contour of the hard palate, and thereby does not substantially obstruct the movement of the user's tongue when the insert is properly disposed into the user's mouth. Such a feature can also increase the interfacial surface tension between the insert and the interior surfaces of the upper mouth. Thus, in some embodiments, the connecting structure comprises a third insert surface configured to contact at least a portion of the hard palate of the user's mouth. In some such embodiments, the connecting structure is configured to contact or conform to at least a portion of the palatal rugae on the surface of the hard palate of the user's mouth. In this context, the term "configured to" has the same meaning as in reference to the such first and second insert surfaces. In some embodiments, the third insert surface is a rigid surface, e.g., a surface that does not conform to take on the shape of surfaces of the user's mouth. Therefore, configuring the surface to contact certain surfaces of a user's mouth (e.g., portions of the palatal rugae) generally involves measuring the contours of certain surfaces of the user's mouth (e.g., by a dental mold) and forming the third insert surface to have a shape that fits to said contours, including the relevant portions of the palatal rugae.

One can also improve the retention of interfacial surface tension by including texture (non-smooth portions), such as grooves or abrasions, on at least a portion of the insert surface. Thus, in some embodiments of any of the aforementioned embodiments, at least a portion of the third insert surface comprises surface texture (or surface topography).

In some embodiments of any of the aforementioned embodiments, the connecting structure is formed from the same material as the first insert surface and the second insert surface, and, in some such embodiments, forms a continuous object with said surfaces. In some embodiments, the connecting structure, including the third surface, is rigid. For example, in some embodiments, the connecting structure has a shore A hardness of at least 40, or a shore A hardness of at least 45, or a shore A hardness of at least 50, or a shore A hardness of at least 55, or a shore A hardness of at least 60, at 25° C. Note that materials that are more suited to hardness measurements using the shore D durometer or the Rockwell test are generally harder than the shore A values recited here, and are therefore included as having a hardness that meets these lower cut-offs. The description of this feature in terms of shore A hardness is not intended to limit the embodiment only to materials whose hardness is suitable for measurement using the shore A durometer.

Because the connecting structure connects the first insert surface and the second insert surface from their respective posterior sides, it does not generally extend beyond the front teeth. Thus, in some embodiments, the connecting structure is configured not to extend in front of the upper teeth when inserted behind the user's upper teeth. Thus, in embodiments, the oral insert is configured not to extend in front of the upper teeth when inserted behind the user's upper teeth.

In embodiments of this aspect, the oral insert comprises a sensing device, wherein the sensing device is in physical communication with the connecting structure. In general, this means that the sensing device is disposed onto or contained by the connecting structure. In some embodiments, the sensing device is disposed onto a surface of the connecting structure. In some other embodiments, the sensing device is contained by the connecting structure. It is generally desirable that the sensing device not move substantially relative to the oral insert. Therefore, in some embodiments, the sensing device is fixed relative to the connecting structure, thereby resisting lateral or rotational movement relative to the connecting structure.

Any sensing device can be used, so long as it is suitable for measuring variables associated with head motion, such as one or more of linear acceleration, rotational acceleration, velocity, displacement, and rotation. In some embodiments, the sensing device comprises one or more sensors for measuring acceleration. In some such embodiments, the devices comprises one or more sensors for (collectively, in the case of multiple sensors) measuring linear and rotational acceleration. In some embodiments, either in addition to or instead of one or more accelerometers or gyroscopes, the sensing device includes one or more of a global positioning system (GPS) sensor, a temperature sensor, such as a thermistor, a sensor for measuring blood pressure, a sensor for measuring pulse, a magnetometer, which measures relative orientation, a sensor for measuring rotational velocity, and the like. In some embodiments, the sensing device comprises one or more accelerometers. In some embodiments, the sensing device comprises a gyroscope. In some embodiments, the sensing device comprises one or more accelerometers and a gyroscope. In some embodiments, this sensing device includes only such biomechanical sensors, such as one or more accelerometers or a gyroscope, and not any other components, such as a power supply, a charger, a processor, a transmitter, or a data storage unit. In such embodiments, such additional devices, such as one or more of a power supply, a charger, a processor, or a data storage unit are disposed remotely from the oral insert and maintain electrical (including electromagnetic) connection to the biomechanical sensing devices in the oral insert via one or more wires or wirelessly. In some other embodiments, however, one or more of these other components, such as a power supply, a charger, a processor, a transmitter, or a data storage unit, can be included within the sensing device that is in physical communication with the connecting structure. In some embodiments, the power supply, whether included within the sensing device or remote from it, is rechargeable, for example by mechanical manipulation, electromagnetic radiation, or by electricity. In some embodiments, the oral insert comprises an outlet, such as a watertight outlet, into which one can insert a plug and place the sensing device (including any optional power supply or data storage unit) in electrical communication with other components remote from the oral insert. Such an outlet can be used to download data from a data storage unit, to charge a power supply, or any number of other uses for which electrical communication with the sensing device may be desirable or convenient.

Figure 5:
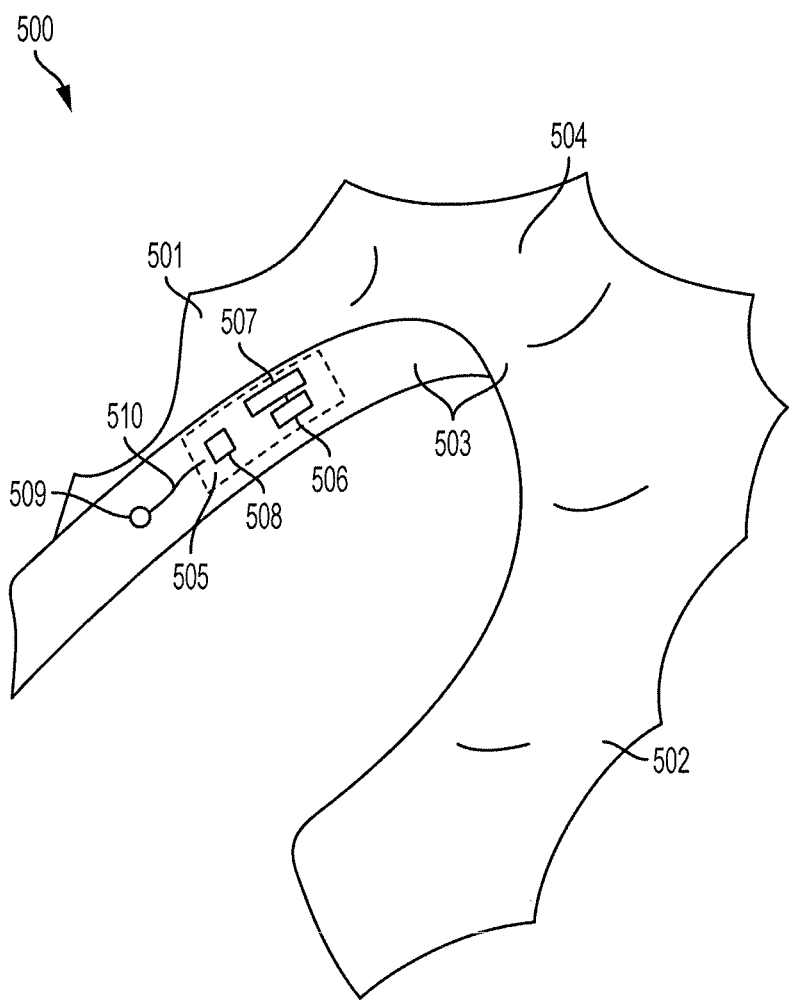
FIG. 5 shows a non-limiting example of an oral insert where the first insert surface and the second insert surface form a continuous surface, and which contains a sensing device.

FIG. 5 shows an example of an oral insert 500 having a first insert surface 501 and a second insert surface 502 and a connecting structure 503 having a third insert surface 504 and a sensing device 505 that includes biomechanical sensors (e.g., one or more accelerometers and/or gyroscopes) 506 and a power source (such as a rechargeable battery) 507 and a data storage unit 508 (such as memory) and a watertight outlet 509 that permits electrical communication with one or more components of the sensing device 505 via wires 510 internal to the connecting structure 503. Other configurations are possible according to any of the above embodiments.

Figure 6:
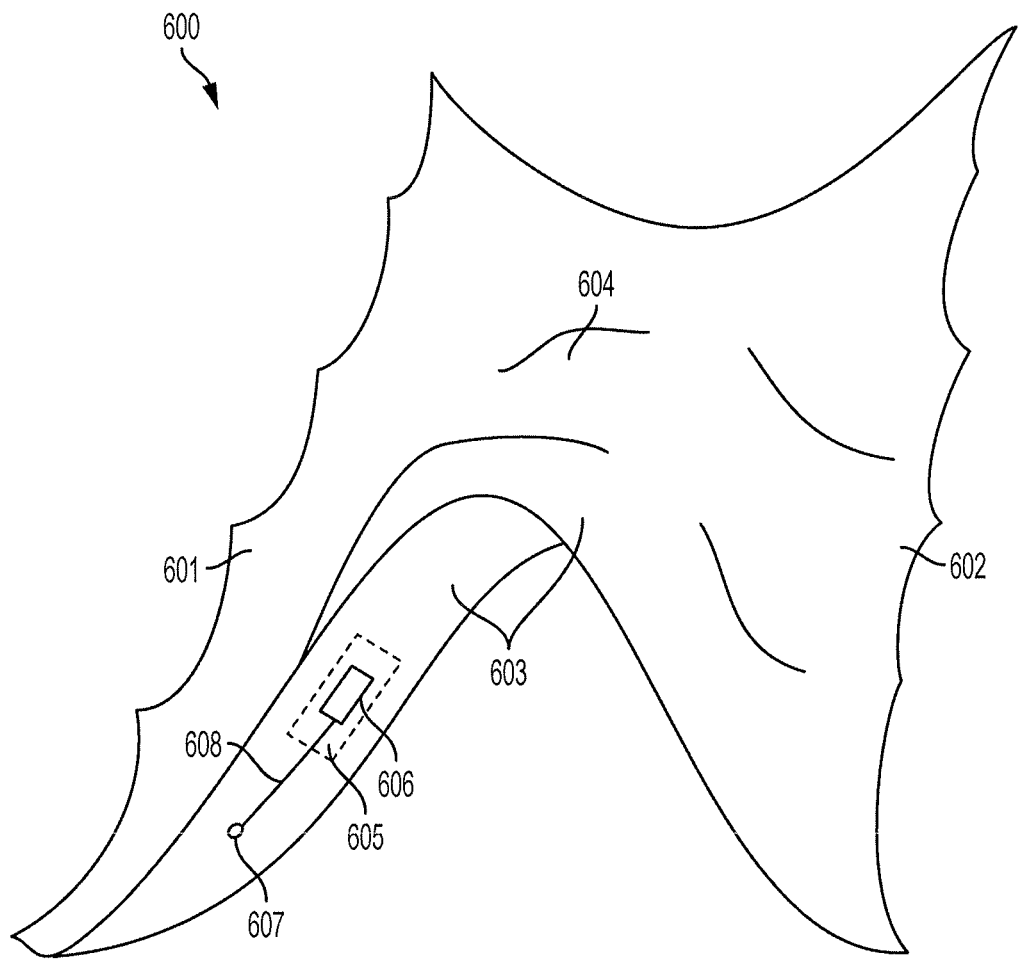
FIG. 6 shows a non-limiting example of an oral insert where the first insert surface and the second insert surface are discontinuous from each other, and which contains a sensing device.

FIG. 6 shows an example of an oral insert 600 having a first insert surface 601 and a second insert surface 602 and a connecting structure 603 having a third insert surface 604 and a sensing device 605 that includes biomechanical sensors (e.g., one or more accelerometers and/or gyroscopes) 606 and a watertight outlet 607 that permits electrical communication with the component of the sensing device 605 via wires 608 internal to the connecting structure 603. Other configurations are possible according to any of the above embodiments.

In general, the oral insert is configured to fit into the region behind the upper teeth of the user's mouth without extending to the outside of the user's teeth and without interfering substantially with the movement of the user's tongue. Thus, in some embodiments, the oral insert is configured not to extend to the outside of the user's front teeth, upon proper insertion into the user's upper mouth. In some embodiments, however, the oral insert comprises one or more clasps (e.g., metal wire clasps) that, for example, are configured to fit one or more of the interproximal spaces between the user's teeth, and which can further assist in holding the oral insert into place. Such clasps can also serve as a means for assisting with removal of the oral insert from the user's mouth. In some such embodiments, the oral insert is configured not to extend to the outside of the user's front teeth, upon proper insertion into the user's upper mouth, except for the extension of the one or more clasps describes above. Moreover, in some embodiments, the oral insert is configured not to extend below the plane formed by the average lowermost point of the user's two maxillary central incisors and the lowermost points of the user's two upper mandibular second molars.

In some embodiments of any of the aforementioned embodiments, it may be desirable to incorporate the oral insert into a bite guard or a mouth guard or bite wings. Thus, in some such embodiments, the oral insert according to any of the aforementioned embodiments is disposed onto a bite guard or a mouth guard or one or more bite wings, either permanently or detachably, in such a manner as not to interfere with insertion of the oral insert behind the user's upper teeth. Moreover, because the insert is generally designed to fit snugly into the cavity of the upper mouth behind the upper teeth, it can, in most circumstances, easily be used in conjunction with various other mouth pieces, whether or not specifically designed to be used in conjunction with the oral insert.

As noted above, the insert can include optional clasps that, among other uses, assist in removing the insert from the user's mouth. The insert can include other features that also assist with removal. For example, in some embodiments, the oral insert comprises one or more small indentations or protrusions, which are manually accessible during normal use. Such small indentations or protrusions can provide a means to assist the user in removing the oral insert from the mouth.

Further, it is generally desirable that the insert avoid contact with any surfaces in the user's mouth that are associated with inducing laryngeal spasms (i.e., a gag reflex). Thus, in some embodiments, the insert is configured not to contact any surfaces of the user's mouth associated with inducing laryngeal spasms, when inserted behind the user's upper teeth.

In certain embodiments of the foregoing, the oral insert conforms well to multiple surfaces of the user's mouth and, by maintaining interfacial surface tension, resists displacement, even when a user endures a substantial impact, such as a hard hit to the head during a sporting event, provides a more accurate measurement of the true motion experienced by the user's head.

Figure 8:
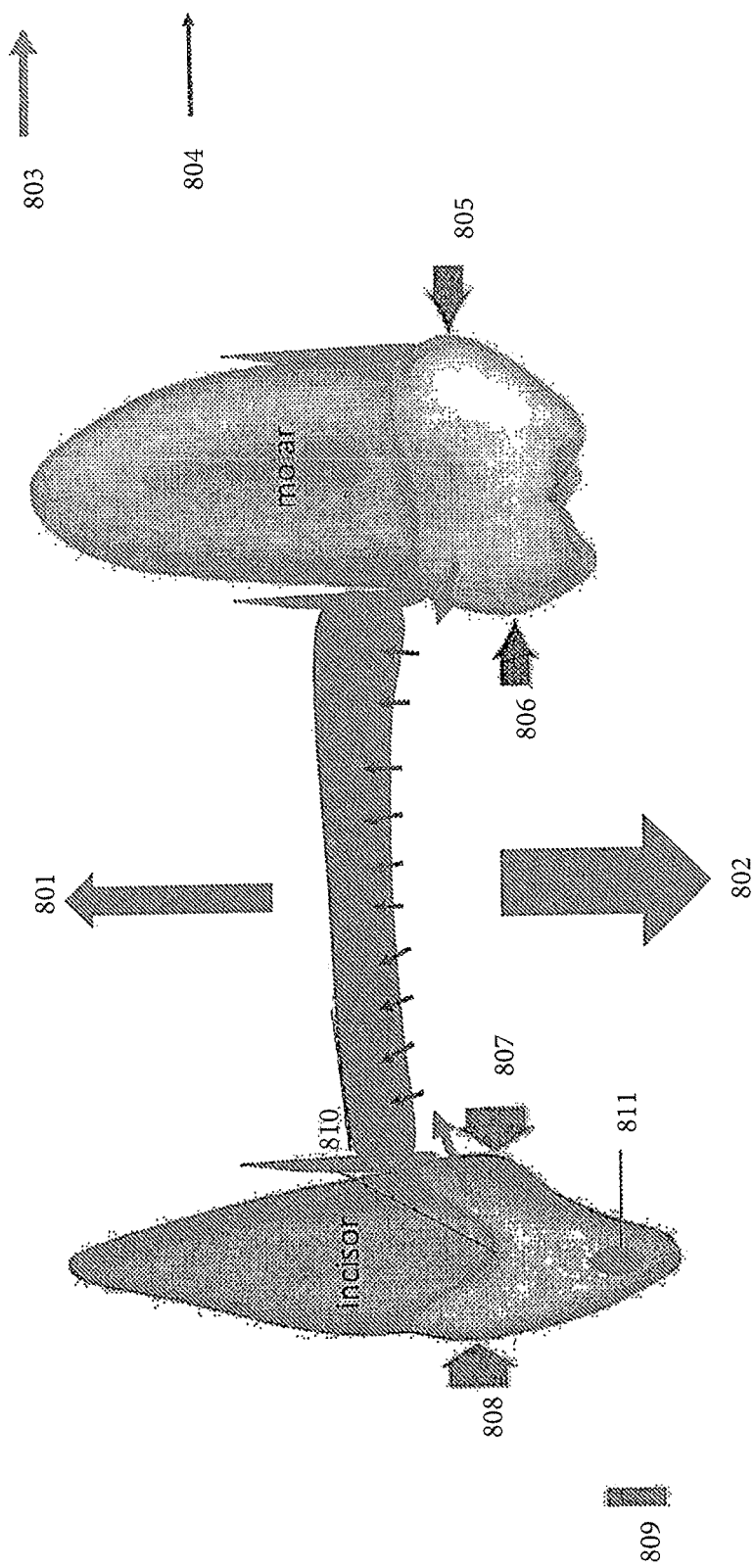
FIG. 8 shows an illustrative depiction of the forces exerted when an oral insert of certain embodiments of the disclosure is disposed in the mouth of a human user.

As a further example of certain embodiments of the oral inserts disclosed herein, FIG. 8 shows an example of the forces that may be present when an oral insert of certain embodiments disclosed herein is placed in the mouth and experiences a force. In the example shown, the oral insert experiences an acceleration 801, which results in a force 802 that wants to pull the insert out of the mouth. The insert experiences certain forces that help to hold it in place, including, but not limited to, mechanical forces 803 and interfacial surface tension forces 804. These latter forces can become very high proportional to the forces exerted from impact and help ensure a good fit and coupling to the user's skull. FIG. 8 also shows the location of the buccal height of contour 805 and the lingual height of contour 806 on a molar. FIG. 8 also shows the locations of the heights of contour 807, 808 on an incisor. FIG. 8 also shows the actual height of contour 809 for the incisor. FIG. 8 also shows the location of the cementoenamel junction 810 and a contact area 811.

Systems Including Oral Inserts and Methods of Use

In at least another aspect, the disclosure provides systems for calculating force experienced by the head of a user, which comprise an oral insert of any of the foregoing aspects or any embodiments thereof.

Figure 7:
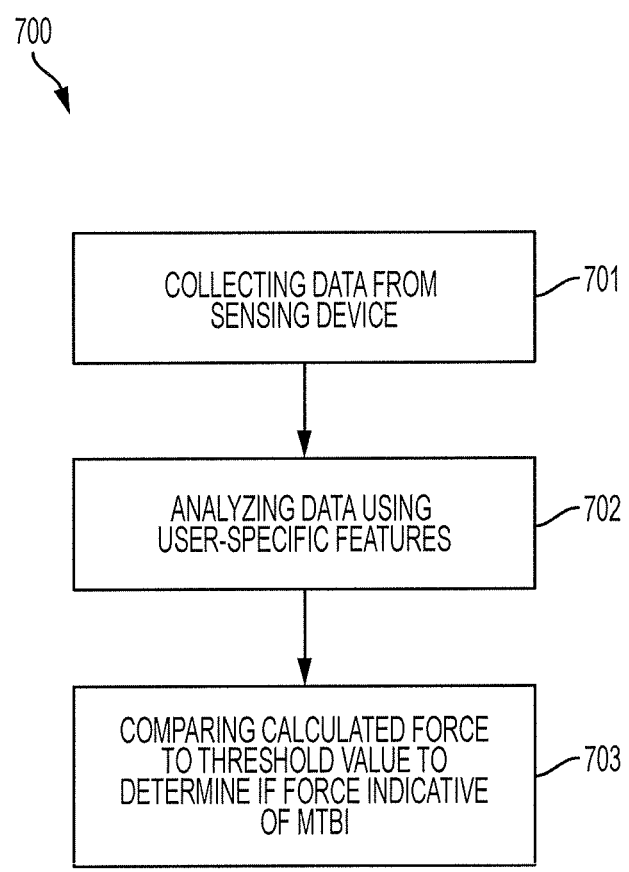
FIG. 7 shows a non-limiting example of an algorithm for calculating or determining whether a user has experienced a force indicative of a concussion or mTBI or increased risk thereof.

As noted above, the oral inserts include a sensing device that can include a number of different components, including, in addition to devices for carrying out the biomechanical sensing (e.g., one or more accelerometers and/or gyroscopes), a power supply, a charger, a processor, a transmitter, or a data storage unit. To the extent that these components are not included in the sensing device itself, they are disposed remotely from the oral insert. In some embodiments, the system further comprises a computer or other processor that is programmed to analyze the data measured by the sensing device and to determine or calculate whether a user's head has experienced a force is indicative of a user's having experienced a concussion or mTBI or increased risk thereof. Such calculations can be carried out by any suitable means. For example, in some embodiments, the data from the sensing device is analyzed with respect to other pre-recorded features of the user's head, including, but not limited to, position of the sensing device relative to the head's center of gravity, mass of the user's head, or other factors, to calculate the force(s) experienced by the user. In some such embodiments, these calculated force(s) are then compared against certain threshold values, which, in some embodiments, can be tailored to specific factors relevant to the user, such as experience of past incidents of mTBI, to determine whether the user has experienced a force indicative of a concussion or mTBI or increased risk thereof. FIG. 7 shows a flow chart for an algorithm 700 for making such a calculation, including collecting data from the sensing device 701, analyzing the data using certain user-specific features to calculate the force(s) experienced by the user 702, and comparing the calculated force(s) against a threshold value (which, in some embodiments, also contains user-specific features) to determine whether the user has experienced a force indicative of a concussion of mTBI or increased risk thereof 703.

In another aspect, the aforementioned systems can also be used in the context of a method for determining the forces experienced by a user's head or a method of determining whether the user has experienced a force to the head indicative of a concussion or mTBI or increased risk thereof. Such methods comprise: providing an oral insert of the first aspect; inserting the oral insert securely behind the upper teeth of a user at a first time; receiving data from the oral insert at a second time, which is later than the first time; and analyzing the data to determine or calculate the force(s) experienced by the user's head from the first time to the second time. In some embodiments, the methods include calculating or determining whether the force calculated using data measured by the oral insert is indicative of a user's having experienced a concussion or mTBI or increased risk thereof, for example, by comparing calculated or determined force(s) experienced by a user's head against a threshold value (which, in some embodiments, also contains user-specific features) which is indicative of the user's having experienced a concussion or mTBI or a risk thereof. Such calculations or determinations are, in some embodiments, made in the manner described above and illustrated in FIG. 7.

Methods for Evaluating Safety Equipment, Safety Procedures, or Game Procedures

In at least another aspect, the disclosure provides methods for assessing the effectiveness of a safety system, the methods comprising: providing an oral insert of any one of the foregoing aspects and embodiments; disposing the oral insert securely to the head of a test subject; protecting the test subject with a safety system; and applying an external force to the test subject while protected with the safety system; and determining the force experienced by the head of the test subject due to the applying of the external force.

In some embodiments, the test subject is a human, and the disposing step comprises inserting the oral insert securely behind the upper teeth of said human. In some other embodiments, the test subject is an anthropomorphic device designed to simulate one or more features of a human, such as a dummy, wherein the one or more features comprises an anthropomorphic head, and the disposing step comprises securing the oral insert to or inside of the anthropomorphic head. The anthropomorphic head need not be shaped exactly like a human head, so long as it possess mechanical features that permit it to simulate the mechanics of a human head.

The disclosure is not limited to any particular external force. The force can be exerted directly to the head, or can be transmitted indirectly to the head via the direct application of a force to another portion of the test subject. Thus, in some embodiments, the external force is a force configured to simulate a blow to the head. In some other embodiments, the external force is a force configured to simulate the effect on the head due to a blow to another part of the body. Any suitable safety system can be used for such testing. Non-limiting examples include: a helmet; a hat, such as a hard hat; a cap; a beanie; an ear guard; a bodily restraint system, such as a lap belt, shoulder restraint, or a combination thereof; a headrest; a seat, such as the seat of a vehicle, an airplane, or a space craft; a protective garment, such as a space suit, a racing suit, or a uniform; and any combinations of the foregoing.

The determining can be carried out according to any of the methods described in the foregoing aspects and embodiments. In some embodiments, the determining step comprises: receiving data from the oral insert following the applying step; and analyzing the data to determine the force experienced by the head of the test subject.

In at least another aspect, the disclosure provides methods for assessing the risk of a procedure for carrying out an activity, the method comprising: providing an oral insert of any of the foregoing aspects and embodiments; disposing the oral insert securely to the head of a test subject; employing the test subject to carry out an activity according to a procedure; and applying an external force to the test subject while carrying out the activity; and determining the force experienced by the head of the test subject due to the applying of the external force.

In some embodiments thereof, the test subject is a human, and the disposing step comprises inserting the oral insert securely behind the upper teeth of said human. In some other embodiments, the test subject is an anthropomorphic device designed to simulate one or more features of a human, such as a dummy, wherein the one or more features comprises an anthropomorphic head, and the disposing step comprises securing the oral insert to or inside of the anthropomorphic head. The anthropomorphic head need not be shaped exactly like a human head, so long as it possess mechanical features that permit it to simulate the mechanics of a human head.

The method can be employed in the context of any activity that can be carried out according to one or more procedures. For example, in some embodiments, the activity is a game, such as a sport, and the procedure is indicative of one or more rules of said game. In some further such embodiments, the game is football (American), soccer, lacrosse, water polo, wrestling, field hockey, ice hockey, baseball, basketball, softball, vehicle racing, martial arts, diving, water skiing, snow skiing, skateboarding, horseback riding, gymnastics, cheerleading, dancing, fitness, golf, trampoline, ice skating, inline skating, motorcycling, snowboarding, ATV-ing, running, or any combination thereof. In some other embodiments, the procedure is a safety procedure. In some such embodiments, the activity is a sport, a game (such as those identified above), an occupational activity, an educational activity, a drill, shopping, any recreational activity, and the like.

The determining can be carried out according to any of the methods described in the foregoing aspects and embodiments. In some embodiments, the determining step comprises: receiving data from the oral insert following the applying step; and analyzing the data to determine the force experienced by the head of the test subject.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. An oral insert for calculating motion experienced by a user's head, the insert comprising:
   a first insert surface configured to contact a first surface of a user's mouth, wherein the first surface of the user's mouth comprises the lingual surface of each of one or more teeth of the upper left side of the user's mouth or the lingual surface of the gums of upper left side of the user's mouth;
   a second insert surface configured to contact a second surface of the user's mouth, wherein the second surface of the user's mouth comprises the lingual surface of each of one or more teeth of the upper right side of the user's mouth or the lingual surface of the gums of the upper right side of the user's mouth;
   a connecting structure, which is in physical communication with the first insert surface and the second insert surface,
   wherein the connecting structure comprises a third insert surface configured to contact and maintain interfacial surface tension with at least a portion of the hard palate of the user's mouth, the oral insert is configured not to extend in front of the upper teeth when inserted behind the user's upper teeth; and
   a sensing device, wherein the sensing device is in physical communication with the connecting structure.

2. The insert of claim 1, wherein the first insert surface is configured to maintain interfacial surface tension with the first surface of the user's mouth.

3. The insert of claim 1, wherein the first insert surface is configured to exert a first expansive force against the first surface of the user's mouth.

4. The insert of claim 1, wherein the second insert surface is configured to maintain interfacial surface tension with the second surface of the user's mouth.

5. The insert of claim 1, wherein the second insert surface is configured to exert a second expansive force against the second surface of the user's mouth.

6. The insert of claim 1, wherein at least one of the first insert surface or the second insert surface is formed from a material having a shore A hardness of at least 40.

7. The insert of claim 1, wherein the third insert surface is configured to contact at least a portion of one or more palatal rugae of the user's mouth.

8. The insert of claim 1, wherein at least a portion of the first insert surface comprises surface texture, or at least a portion of the second insert surface comprises surface texture, or at least a portion of the third insert surface comprises surface texture.

9. The insert of claim 1, wherein the connecting structure is configured not to extend in front of the user's upper teeth when inserted behind the user's upper teeth.

10. The insert of claim 1, wherein the sensing device is contained by the connecting structure.

11. The insert of claim 1, wherein the sensing device comprises one or more gyroscopes, or one or more accelerometers, or any combination thereof.

12. The insert of claim 11, wherein the one or more accelerometers measure linear acceleration, rotational acceleration, or any combination thereof.

13. The insert of claim 11, wherein the one or more accelerometers are fixed relative to the connecting structure, so as to resist lateral or rotational movement relative to the connecting structure.

14. The insert of claim 11, wherein the one or more accelerometers are fixed relative to the connecting structure, so as to maintain a constant displacement relative to the center of gravity of the user's head.

15. The insert of claim 1, wherein the insert is configured not to contact any surfaces of the user's mouth associated with inducing laryngeal spasms when inserted behind the user's upper teeth.

16. A method of determining a force experienced by the head of a user, the method comprising:
   providing an oral insert of claim 1, wherein the sensing device comprises or is in communication with one or more of a processor, a transmitter, and a data storage unit;
   inserting the oral insert securely behind the upper teeth of the user at a first time;
   receiving from the sensing device in the oral insert measurements of linear and rotational acceleration kinematics associated with head motion at a second time, which is later than the first time; and
   calculating the force experienced by the head of the user from the first time to the second time based on the measurements of linear and rotational acceleration kinematics associated with head motion.

17. A method for assessing a safety system's effectiveness, the method comprising:
   providing an oral insert of claim 1;
   disposing the oral insert securely to the head of a test subject;
   protecting the test subject with a safety system;
   applying an external force to the head of the test subject while protected with the safety system; receiving from the sensing device measurements of linear and rotational acceleration kinematics associated with head motion due to the applying of the external force; and
   calculating a force experienced by the head of the test subject based on the measurements of linear and rotational acceleration kinematics associated with head motion.

* * * * *